(12) United States Patent
Notten et al.

(10) Patent No.: US 12,239,486 B2
(45) Date of Patent: Mar. 4, 2025

(54) ULTRASOUND IMAGING SYSTEM USING AN ARRAY OF TRANSDUCER ELEMENTS AND AN IMAGING METHOD

(71) Applicant: KONINKLIJKE PHILIPS N.V., Eindhoven (NL)

(72) Inventors: Marc Godfriedus Marie Notten, Elsloo (NL); Peter Dirksen, Hilversum (NL); Nico Maris Adriaan de Wild, Eindhoven (NL); Rüdiger Günter Mauczok, Erkelenz (DE); Antonia Cornelia van Rens, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1030 days.

(21) Appl. No.: 17/260,346

(22) PCT Filed: Jul. 17, 2019

(86) PCT No.: PCT/EP2019/069287
§ 371 (c)(1),
(2) Date: Jan. 14, 2021

(87) PCT Pub. No.: WO2020/016323
PCT Pub. Date: Jan. 23, 2020

(65) Prior Publication Data
US 2021/0282749 A1    Sep. 16, 2021

(30) Foreign Application Priority Data
Jul. 18, 2018   (EP) ..................................... 18184192

(51) Int. Cl.
*A61B 8/00*   (2006.01)
*B06B 1/02*   (2006.01)

(52) U.S. Cl.
CPC .......... *A61B 8/4494* (2013.01); *A61B 8/4444* (2013.01); *B06B 1/0207* (2013.01); *B06B 1/0292* (2013.01); *B06B 2201/76* (2013.01)

(58) Field of Classification Search
None
See application file for complete search history.

(56) References Cited

U.S. PATENT DOCUMENTS

| 4,359,767 A | 11/1982 | Sachs et al. |
| 2003/0048698 A1* | 3/2003 | Barnes .................. B06B 1/0292 367/181 |

(Continued)

OTHER PUBLICATIONS

International Search Report and Written Opinion for International Application No. PCT/EP2019/069287, filed Jul. 17, 2019, 13 pages.

*Primary Examiner* — Katherine L Fernandez

(57) ABSTRACT

The invention provides an ultrasound imaging system, comprising an array of transducer elements grouped into element groups, wherein the element groups comprise a plurality of first element groups (having a first orientation) and a plurality of second element groups (having a second orientation different from the first orientation). A first conductor is connected to each of the elements in each first element grouping and a second conductor is connected to each of the elements in each second element grouping. Each element group is adapted to be activated for transmission or reception by the application of a bias voltage, by way of a plurality of bias voltage circuits, and controlled by a plurality of transmit and receive circuits. The system is adapted to acquire first ultrasound data, wherein the bias voltage is applied to the first conductors of the array (or a sub-array) and the transducers receive a signal from a transmit and receive circuit. The system is further adapted to acquire second ultrasound data, wherein the bias voltage is applied to the second conductors of the array (or a different sub- (Continued)

array) and the transducers receive a signal from a transmit and receive circuit. Thus, the ultrasound system is adapted to acquire two separate ultrasound data (such as ultrasound images) corresponding to different views without requiring any physical movement of the array.

2 Claims, 11 Drawing Sheets

(56) References Cited

U.S. PATENT DOCUMENTS

| | | |
|---|---|---|
| 2004/0160144 A1* | 8/2004 | Daft .................... G01S 15/8925 |
| | | 310/334 |
| 2007/0079658 A1* | 4/2007 | Wagner ................ B06B 1/0207 |
| | | 600/437 |
| 2012/0179043 A1 | 7/2012 | Kim et al. |
| 2014/0060196 A1 | 3/2014 | Falter et al. |
| 2016/0310992 A1 | 10/2016 | Van Rens et al. |
| 2018/0015504 A1* | 1/2018 | Zhao .................... B06B 1/0292 |
| 2018/0372691 A1* | 12/2018 | Zhao ................. G01N 29/2406 |

* cited by examiner

ULTRASOUND IMAGING SYSTEM USING AN ARRAY OF TRANSDUCER ELEMENTS AND AN IMAGING METHOD

RELATED APPLICATIONS

This application is the U.S. National Phase application under 35 U.S.C. § 371 of International Application No. PCT/EP2019/069287, filed on Jul. 17, 2019, which claims the benefit of and priority to European Application No. 18184192.5, filed Jul. 18, 2018, which is incorporated by referenced in its entirety.

FIELD OF THE INVENTION

This invention relates to an ultrasound imaging system using an array of transducer elements, in particular capacitive micromachined ultrasound transducer (CMUT) elements.

BACKGROUND OF THE INVENTION

FIG. 1 shows a typical imaging workflow 1, in this example used to perform vascular imaging, which employs an ultrasound patch 2 (in this example a low profile ultrasound probe) in procedures requiring visual guidance to aid the insertion of a needle. To enable optimal image guidance support it is important to have a multiple views of the region of interest 3. In some cases, a single 2D view may not provide sufficient visual guidance and it may be necessary to have both the cross sectional and longitudinal view of the region of interest.

There are several methods for capturing both views with a conventional 2D transducer: however, this requires manual movement of the transducer by 90 degrees which may result in losing the reference starting position of the initial image.

Another option is to place two CMUT transducers orthogonally to each other. In this case it is possible to create the two views; however, there would be a physical distance between both transducers, which will result in the views being misaligned.

There is therefore a need for a system which enables use of an array of ultrasound elements to generate multiple views of an imaging area having different orientations but which maintains the same imaging reference point across multiple images, without requiring significant additional hardware.

Document US 2016/0310992 discloses a three electrode CMUT cell providing an ultrasound transducer with two actively driven electrodes.

SUMMARY OF THE INVENTION

The invention is defined by the claims.

According to examples in accordance with an aspect of the invention, there is provided an ultrasound system, comprising:
an array of transducer elements grouped into element groups, wherein the element groups comprise:
a plurality of first element groups having a first orientation; and
a plurality of second element groups having a second orientation, different from the first orientation;
a set of first conductors with a first conductor shared between elements in each first element group and a set of second conductors with a second conductor shared between elements in each second element group:
a first plurality of bias voltage circuits; and
a second plurality of transmit and receive circuits:
wherein each element group is adapted to be activated for transmission or reception by the application of a bias voltage from a bias voltage circuit and controlled by a transmit and receive circuit,
wherein the system is adapted to acquire:
first ultrasound data in which the element groups of the array, or the element groups of a sub-array of the element groups, are activated by a bias voltage circuit via a first conductor; and
second ultrasound data in which the element groups of the array, or the element groups of a sub-array of the element groups, are activated by a bias voltage circuit via a second conductor
and wherein a first element group and a second element group are activated simultaneously, thereby simultaneously acquiring the first ultrasound data and second ultrasound data.

This system is able to provide a biplane view of a region of interest without the need to physically move the system. Instead, first ultrasound data is based on first element group actuation propagating in a first direction according to the first orientation and second ultrasound data is based on second element group actuation propagating in a second direction according to the second orientation. The ultrasound data are be obtained at the same time, thereby generating a simultaneous bi-plane view of a region of interest.

The term simultaneous refers to the activating of the first element group and the second element group at the same time, which results in the concurrent acquisition of first and second ultrasound data.

In the case of ultrasound imaging, the first ultrasound data may be used to generate a first ultrasound image. The orientation of the imaging plane of the first image will be associated with the first orientation of the first element groups. Similarly, the second ultrasound data may be used to generate a second ultrasound image, the orientation of which may be associated with the second orientation of the second element groups. Thus, the system may be used to acquire bi-plane ultrasound images without the need to physically maneuver the probe between image acquisitions.

Alternatively, the ultrasound data may be used to determine analytical signals indicative of a given physiological process, for example hemodynamic monitoring. In this case, the dynamics of the blood flow in the region of interest may be viewed in a bi-plane manner as described above. The ultrasound data may be used to acquire a bi-plane view of any suitable process.

By way of example, the full array of element groups, which may in this case be CMUT elements, may be fired with the bias voltage applied to the first conductors and the transmit receive circuit connected to the second conductors followed by the full array being fired with the bias voltage applied to the second conductors and the transmit and receive circuit connected to the first conductors. Thus, first and second ultrasound data representing differing views are collected whilst the array of transducer elements remains stationary.

Alternatively, a first sub-array of the element groups, a sub-array referring to any collection of the element groups smaller than the full array, may be activated by the bias voltage circuits via the first conductors and connected to the transmit and receive circuits by way of the second conductors in order to generate first ultrasound data. A second sub-array of the element groups, which may or may not overlap with the first sub-array, may be activated by bias voltage circuits via of the second conductors and connected to the transmit and receive circuits by way of the first conductors in order to generate second ultrasound data having a different view to the first ultrasound data.

Thus, it is possible to generate, in the example of an ultrasound imaging system, a first image, for example having a cross sectional view of an imaging region, and a second image, for example having a longitudinal view of the imaging region, whilst reducing or eliminating any movement of the transducer array between capturing the two images.

The first and second element groups of the transducer elements refer to transducer elements that share a connection with a common first and second conductor, respectively. Further, each individual transducer element will belong to both a first element group and a second element group by way of a connection to a first conductor and a second conductor, respectively. The transducer elements themselves may be physically arranged into rows and columns on the transducer die: however, the transducers may also be arranged in alternate patterns, such as dense packing or hexagonal packing arrangements.

In an embodiment, an angle between the first orientation and the second orientation is: 90 degrees: 60 degrees: 45 degrees: 30 degrees: or 0 degrees.

The first and second orientations may be varied according to the application of the system in order to obtain the optimal view of the region of interest.

In an arrangement, the first element groups and the second element groups are arranged in a Fishbone layout.

The Fishbone layout allows the first and second element groups to be arranged at an optimal angle to each other on a per application basis.

In an embodiment, the system is further adapted to acquire, time sequentially:
  first ultrasound data in which all of the transducer elements of the array are activated by a bias voltage circuit via a first conductor and connected to a transmit and receive circuit via a second conductor; and
  second ultrasound data in which all of the transducer elements of the array are activated by a bias voltage circuit by a second conductor and connected to a transmit and receive circuit via a first conductor.

In this embodiment, the whole transducer array is used to form the first and second ultrasound data groups, in a time sequential manner. Thus, the full resolution of the transducer array is used for each image, and there is perfect positional overlap between the two data groups in addition to the simultaneously acquired bi-plane data.

In some embodiments, each first conductor is associated with a first switch which selectively connects the row conductor to a bias voltage circuit or to a transmit and receive circuit, and each second conductor is associated with a second switch which selectively connects the column conductor to a bias voltage circuit or to a transmit and receive circuit.

The first and second switches enable the functions of the first element groups and second element groups to be switched around, respectively. In the case of an ultrasound imaging system, image slices are formed based on the line of transducer elements, defined by the element groups, which connect to a transmit and receive circuit, and the switching enables two sets of orthogonal image slices to be formed. The switch may be implemented using hardware or software methods.

In some embodiments, each first conductor is associated with a first circuit, said circuit is arranged to connect the first conductor to a bias voltage circuit through an inductor and to a transmit and receive circuit through a capacitor, and each second conductor is associated with a second circuit, said circuit is arranged to connect the second conductor to a bias voltage circuit through an inductor and to a transmit and receive circuit through a capacitor.

The first and second circuits avoid the need for switching operations, since each first and second element group is coupled to both a bias voltage circuit and to a transmit and receive circuit.

In an arrangement, the system is adapted to generate:
  first ultrasound data in which the element groups of a first sub-array of the element groups are activated by a bias voltage circuit via a first conductor and connected to a transmit and receive circuit; and
  second ultrasound data in which the element groups of a second sub-array of the element groups are activated by a bias voltage circuit via a second conductor and connected to a transmit and receive circuit.

In this example, different areas of the transducer array are employed for different data acquisition orientations. The bias voltage circuit and transmit and receive circuit may be connected to the same conductors or else the transmit and receive circuit may be connected to the opposite conductor to the bias circuit. In this way, both orientations may be available to the user during the data acquisition.

In a further arrangement, the first sub-array comprises a first and second region, and the second sub-array comprises a third region disposed between the first and second regions.

In this way, the two areas from which ultrasound data is acquired are interleaved.

In some designs, all of the transducer elements are connected permanently to the plurality of bias voltage circuits, and plurality of transmit and receive circuits are switchable between the first and second sub-arrays.

In an arrangement, each transducer element comprises one or more CMUTs.

According to examples in accordance with an aspect of the invention, there is provided an ultrasound arrangement comprising:
  a first system as described above; and
  a second system as described above, comprising:
    a plurality of first element groups of the second system having a first orientation; and
    a plurality of second element groups of the second system having a second orientation, different from the first orientation of the second system, wherein the first and second orientations of the first and second element groups of the second system are different to the first and second orientations of the first and second element groups of the first system.

In this way, it is possible to contain two bi-plane transducer arrays within the same arrangement, thereby increasing the number of view available to the user.

In an embodiment, the systems or arrangements described above may comprise an ultrasound probe.

According to examples in accordance with an aspect of the invention, there is provided an ultrasound imaging method for performing ultrasound data acquisition using an array of transducer elements grouped into element groups with a set of first conductors with a first conductor shared between elements in each of a plurality of first element groups, having a first orientation, and a set of second conductors with a second conductor shared between elements in each of a plurality of second element groups, having a second orientation different from the first, wherein the method comprises:

generating first ultrasound data by connecting the element groups of the array or the element groups of a sub-array of the element groups to a bias voltage circuit by a first conductor; and generating second ultrasound data by connecting the element groups of the array or the element groups of a sub-array of the element groups to a bias voltage circuit by a second conductor.

In an embodiment, the method comprises generating time sequentially:

first ultrasound data in which all of the transducer elements of the array are activated by a bias voltage circuit via a first conductor and connected to a transmit and receive circuit via second conductor; and second ultrasound data in which all of the transducer elements of the array are activated by a bias voltage circuit via a second conductor and connected to a transmit and receive circuit by a first conductor; and activating a first element group and a second element group simultaneously, thereby simultaneously generating the first ultrasound data and the second ultrasound data.

In an embodiment, the method further comprises generating:

first ultrasound data in which the element groups of a first sub-array of the element groups are activated by a bias voltage circuit via a first conductor and connected to a transmit and receive circuit; and second ultrasound data in which the element groups of a second sub-array of the element groups are activated by a bias voltage circuit via a second conductor and connected to a transmit and receive circuit.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
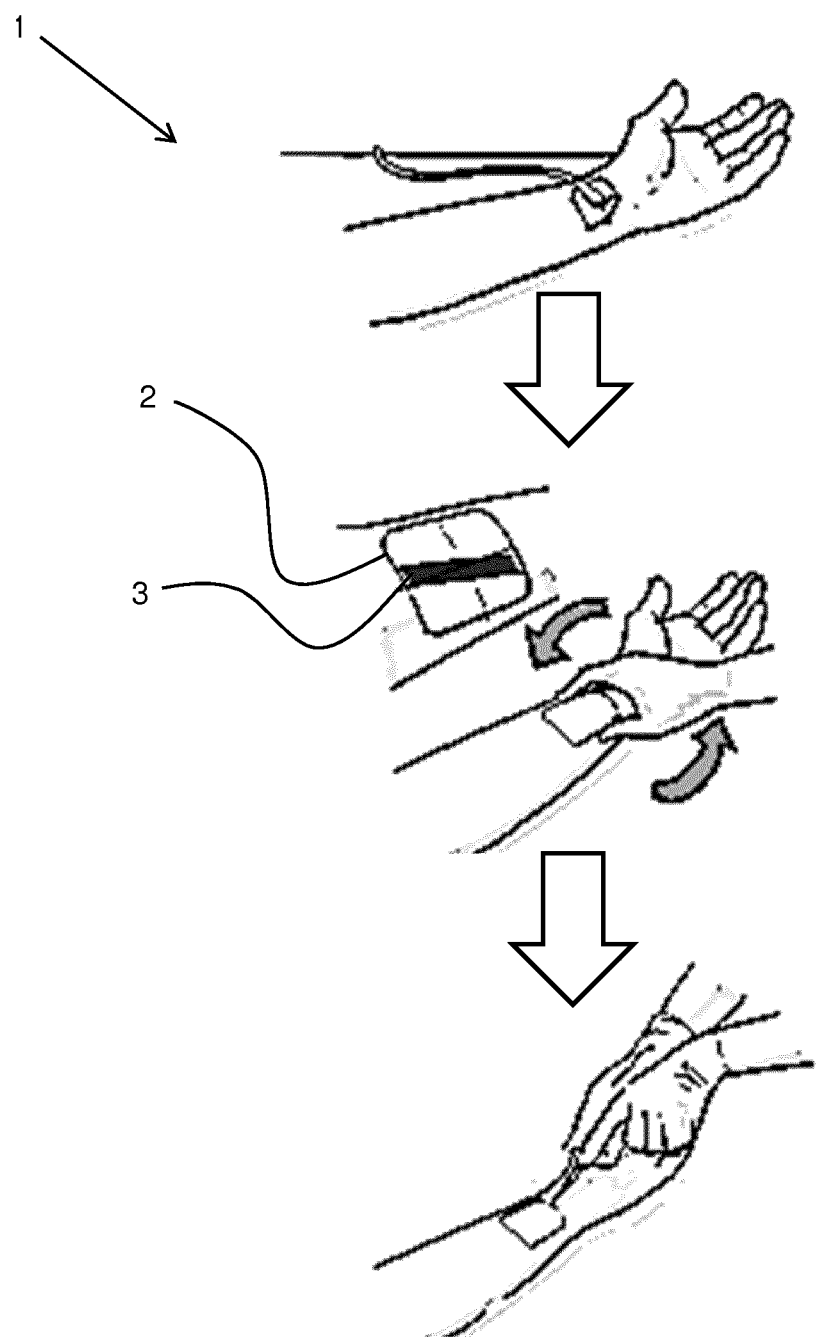
FIG. 1 shows a possible imaging workflow.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound imaging system, comprising an array of transducer elements grouped into element groups, wherein the element groups comprise a plurality of first element groups (having a first orientation) and a plurality of second element groups (having a second orientation different from the first orientation). A first conductor is connected to each of the elements in each first element grouping and a second conductor is connected to each of the elements in each second element grouping. Each element group is adapted to be activated for transmission or reception by the application of a bias voltage, by way of a plurality of bias voltage circuits, and controlled by a plurality of transmit and receive circuits. The system is adapted to acquire first ultrasound data, wherein the bias voltage is applied to the first conductors of the array (or a sub-array) and the transducers receive a signal from a transmit and receive circuit. The system is further adapted to acquire second ultrasound data, wherein the bias voltage is applied to the second conductors of the array (or a different sub-array) and the transducers receive a signal from a transmit and receive circuit. The system is adapted to acquire the first and second ultrasound data simultaneously. Thus, the ultrasound system is adapted to acquire two separate ultrasound data (such as ultrasound images) corresponding to different views without requiring any physical movement of the array.

Figure 2:
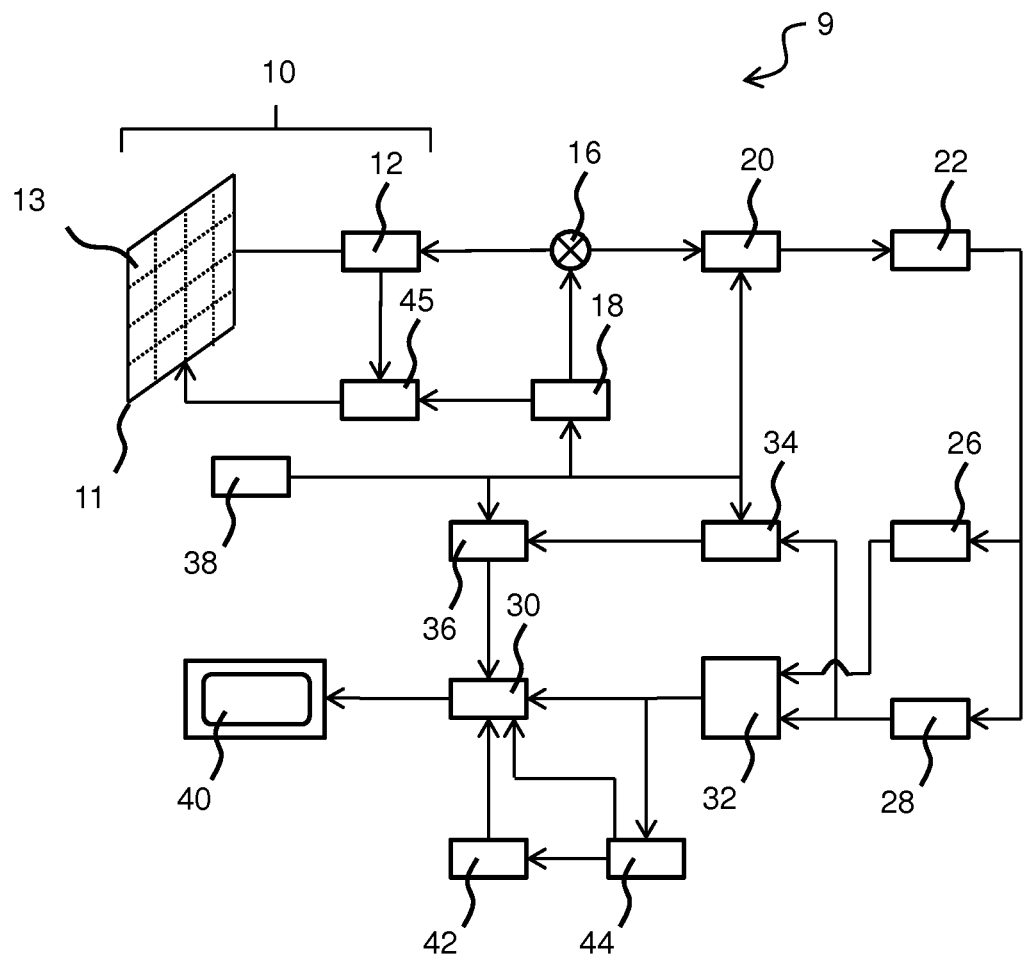
FIG. 2 shows an ultrasound imaging system to explain the general operation.

The general operation of an exemplary ultrasound (imaging) system 9 will first be described, with reference to FIG. 2, and with emphasis on the signal processing function of the system.

The general operation of an exemplary ultrasound system will first be described, with reference to FIG. 2, and with emphasis on the signal processing function of the system since this invention relates to the processing of the signals measured by the transducer array.

The system comprises an array transducer probe 10 which has a transducer array 11 for transmitting ultrasound waves and receiving echo information. The transducer array 11 may comprise CMUT transducers: piezoelectric transducers, formed of materials such as PZT or PVDF: or any other suitable transducer technology. In this example, the transducer array 11 is a two-dimensional array of transducers comprising a CMUT cell 13 capable of scanning either a 2D plane or a three dimensional volume of a region of interest. In another example, the transducer array may be a ID array.

The transducer array 11 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects a main beamformer 20 from high energy transmit signals in the case where a microbeamformer is not used and the transducer array is operated directly by the main system beamformer. The transmission of ultrasound beams from the transducer array 11 is directed by a transducer controller 18 coupled to the microbeamformer by the T/R switch 16 and a main transmission beamformer (not shown), which can receive input from the user's operation of the user interface or control panel 38. The transducer controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to the main beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering: decimation: I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 2 only the microbeamformer 12 and the main beamformer 20 are shown, for simplicity. In the complete system, there will also be a transmission chain with a transmission micro beamformer, and a main transmission beamformer.

The function of the microbeamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 11 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction: posterior enhancement, for example caused by a weak attenuator: reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the control panel 38, such as the point in the anatomy of an image where a measurement is to be made.

Output data from the quantification processor is coupled to a graphics processor 36 for the reproduction of measurement graphics and values with the image on the image display 40, and for audio output from the image display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the control panel 38, such as patient name. The user interface is also coupled to the transmit transducer controller 18 to control the generation of ultrasound signals from the transducer array 11 and hence the images produced by the transducer array and the ultrasound system. The transmit control function of the transducer controller 18 is only one of the functions performed. The transducer controller 18 also takes account of the mode of operation (given by the user) and the corresponding required transmitter configuration and band-pass configuration in the receiver analog to digital converter. The transducer controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 3:
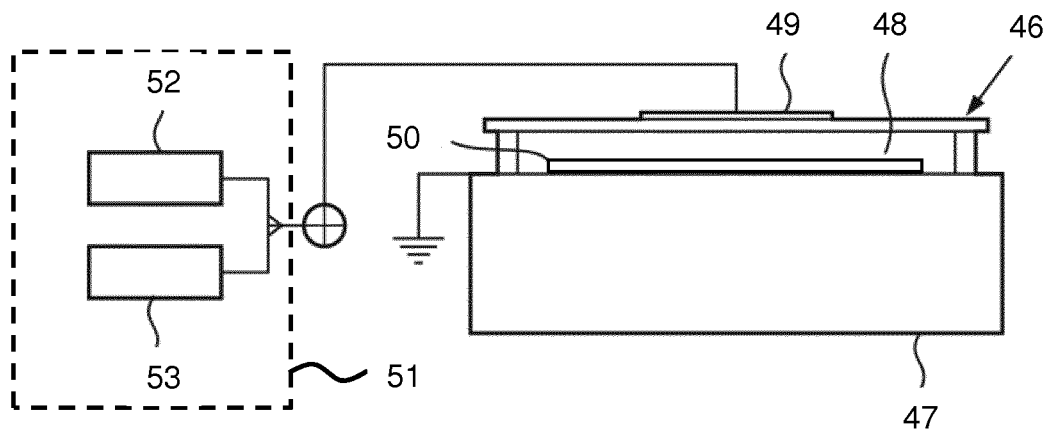
FIG. 3 schematically depicts a typical CMUT cell of an ultrasound system operable in a collapsed mode.

FIG. 3 shows a transducer element in the form of a CMUT cell for use in an array to form the ultrasound probe.

Such a CMUT cell 13 typically comprises a flexible membrane or diaphragm 46 suspended above a silicon substrate 47 with a gap or cavity 48 therebetween. A first electrode 50 is located on the floor of the cell on the upper surface of the silicon substrate 47 in this example. A second electrode 49 is located on the flexible membrane 46 and moves with the diaphragm. In the example shown, the two electrodes are circular.

A dielectric (not shown) is provided on the silicon substrate 47 and underneath the top (second) electrode 49. These two dielectrics may be equal in composition and thickness, but may be also asymmetric (different materials and thicknesses).

Other realizations of the second electrode 49 design can be considered, such as second electrode 49 may be embedded in the flexible membrane 46 or it may be deposited on the flexible membrane 46 as an additional layer. In this example, the first electrode 50 is circularly configured and embedded in the silicon substrate 47 by way of non-limiting example. Other suitable arrangements, e.g. other electrode shapes and other locations of the first electrode 50, e.g. on the silicon substrate 47 such that the first electrode 50 is directly exposed to the gap 48 or separated from the gap 48 by an electrically insulating layer or film to prevent a short-circuit between the second electrode 49 and the first electrode 50. In addition, the flexible membrane 46 is fixed relative to the top face of the silicon substrate 47 and configured and dimensioned so as to define a spherical or cylindrical gap 48 between the flexible membrane 46 and the silicon substrate 47.

It is noted for the avoidance of doubt that in FIG. 3 the first electrode 50 is grounded by way of non-limiting example. Other arrangements, e.g. a grounded second electrode 49 or both second electrode 49 and first electrode 50 floating are of course equally feasible.

The CMUT cell 13 and its gap 48 may exhibit alternative geometries. For example, gap 48 could exhibit a rectangular or square cross-section, a hexagonal cross-section, an elliptical cross-section, or an irregular cross-section. Herein, reference to the diameter of the CMUT cell 13 shall be understood as the biggest lateral dimension of the cell.

In FIG. 3, the diameter of the cylindrical gap 48 is larger than the diameter of the circularly configured first electrode 50. Second electrode 49 may have the same outer diameter as the circularly configured first electrode 50, although such conformance is not required and FIG. 3 shows a larger first electrode 50. Thus, the second electrode 49 may be fixed relative to the top face of the flexible membrane 46 so as to align with the first electrode 50 below: The electrodes of the CMUT cell 13 provide the capacitive plates of the device and the gap 48 is the dielectric between the plates of the capacitor. When the diaphragm vibrates, the changing dimension of the dielectric gap between the plates provides a changing capacitance which is sensed as the response of the CMUT cell 13 to a received acoustic echo. The gap 48 of the CMUT cell may have a shape other than the cylindrical shape such as rectangular, hexagonal or pentagonal shapes.

The spacing between the electrodes is controlled by applying a static voltage, e.g. a DC bias voltage, to the electrodes with a voltage supply 51. The voltage supply 51 may optionally comprise separate stages 52, 53 for providing the DC and AC or stimulus components respectively of the drive voltage of the CMUT cells 13, e.g. in transmission mode. The first stage 52 may be adapted to generate the static (DC) voltage component which is known as the bias voltage and the second stage 53 may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold voltage for forcing the CMUT cells 13 into their collapsed states. This has the advantage that the first stage 52 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component.

Other suitable embodiments of the voltage supply 51 should be apparent, such as for instance an embodiment in which the voltage supply 51 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage supply 51 may be implemented in any suitable manner.

It is known that by applying a static voltage above a certain threshold, the CMUT cell 13 is forced into a collapsed state in which the flexible membrane 46 collapses onto the silicon substrate 47. This threshold value may depend on the exact design of the CMUT cell 13 and is defined as the DC bias voltage, known as the collapse voltage, at which the flexible membrane 46 sticks to (contacts) the cell floor through the force due to the electric field between the electrodes. The amount (area) of contact between the flexible membrane 46 and the silicon substrate 47 is dependent on the applied bias voltage. Increasing the contact area between the flexible membrane 46 and the silicon substrate 47 increases the resonant frequency of the flexible membrane 46.

The frequency response of a collapsed mode CMUT cell 13 may be varied by adjusting the DC bias voltage applied to the CMUT electrodes after collapse. As a result, the resonant frequency of the CMUT cell increases as a higher DC bias voltage is applied to the electrodes.

FIG. 3 shows the CMUT cell with one grounded electrode and one signal electrode. Instead, the bias voltage may be applied on one electrode and the AC stimulus may be applied to the other.

Figure 4:
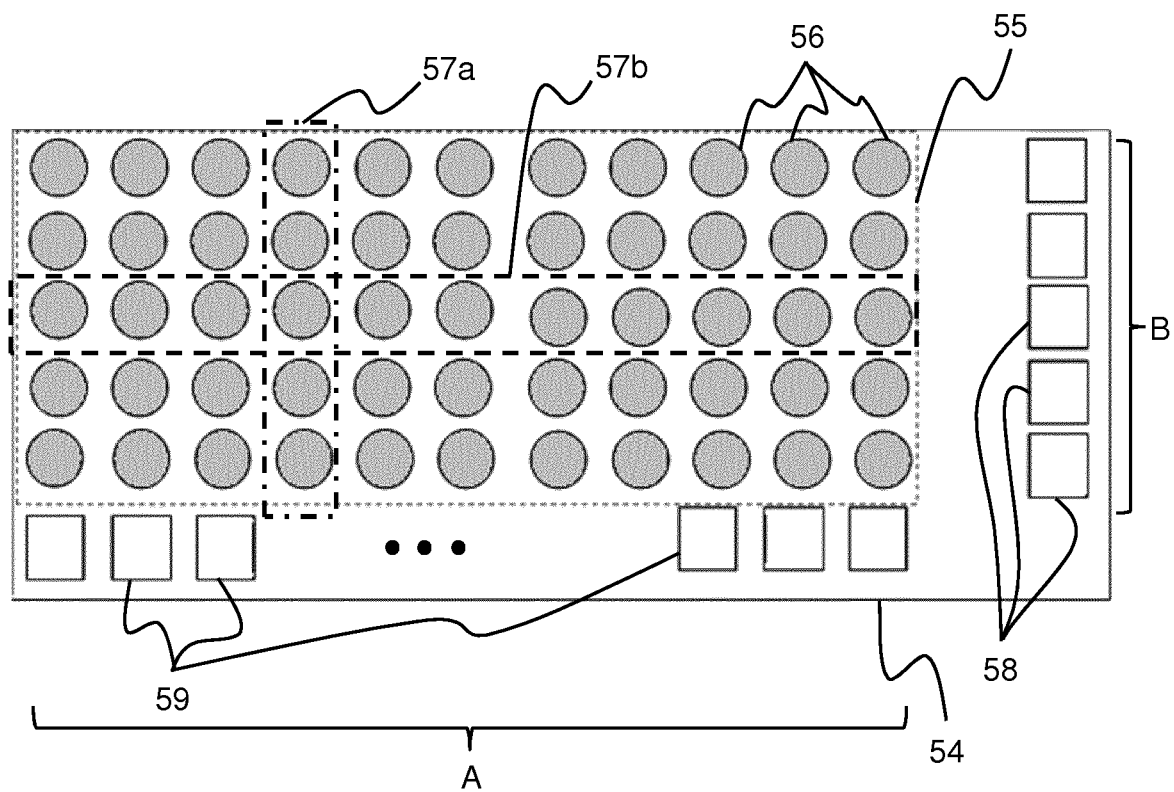
FIG. 4 shows a schematic representation of a transducer die.

FIG. 4 shows a schematic of a transducer die 54 having an array 55 of transducers 56. The transducer array shown in this Figure is arranged in a simple square grid: however, it is also possible to arrange the transducer array in alternate patterns, such as a hexagonal or dense packing pattern as described with reference to FIG. 6b below.

The transducers 56 of the transducer array 55 may be grouped into first element groups 57a having a first orientation and second element groups 57b having a second orientation different to the first. In the example shown in FIG. 4, the first and second orientations are orthogonal to each other: however, the first and second orientations may be at any angle according to what is required in a given application of the system.

In addition, the transducer die 54 may comprise a plurality of first circuits 58 and a plurality of second circuits 59, which may be connected to the bias voltage circuits and/or the transmit and receive circuits and are connected to the transducers 56 as described below: In some arrangements, the bias voltage circuits may be connected to the first circuits located on one side of the array such as side B in this example and the transmit and receive circuits may be connected to the second circuits located on another of the array such as side A. In other arrangements, the bias voltage circuits may be connected to the second circuits located on side A and the transmit and receive circuits may be connected to the first circuits located on side B. Alternatively, the first circuits 58 and second circuits 59 may be connected to both the bias voltage circuit and the transmit and receive circuits and switch between supplying the bias voltage and the transmit and receive signals at side A or side B according to the desired operation of the transduce die. The operation of the first and second circuits is described further below with reference to FIGS. 11 and 12.

In the case where the transducers are CMUTs, the bias voltage will cause the drum of the transducer cell to enter a collapsed mode and the transmit signals will cause the collapsed drum to vibrate. The returning vibrations will then be received as receive signals and processed to form the ultrasound image.

Figure 5:
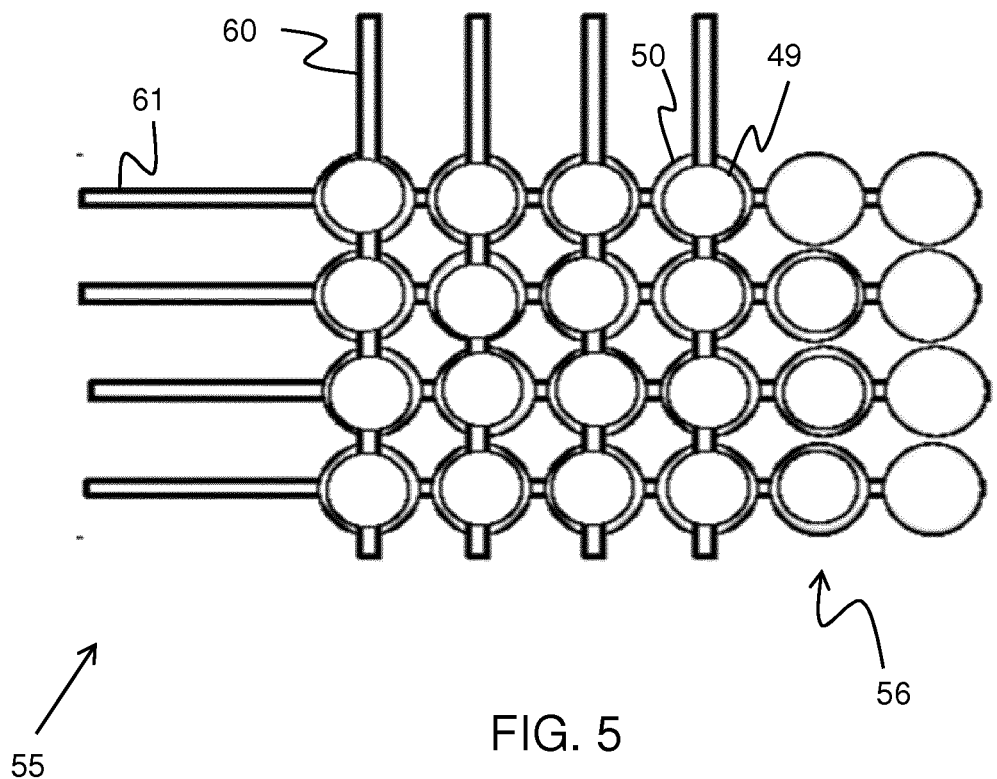
FIG. 5 shows a schematic representation of the first ultrasonic imaging array comprising CMUTs.

FIG. 5 shows an example of the ultrasonic transducer array 55 wherein the transducers 56 are CMUTs, which comprise and second electrode 49 and a first electrode 50.

The operation of the transducer array as a bi-plane imaging system will now be described. As stated above, a CMUT comprises an upper and lower electrode. These electrodes are separated by a cavity, wherein the bottom electrode is fixed at one side of the cavity and the upper electrode is suspended at the opposite side of the cavity by way of a flexible membrane. When a bias voltage is supplied to one of the electrodes, they are brought together and the flexible membrane enters a depressed state. In this state, the membrane can be made to vibrate at ultrasonic frequencies by supplying a radio frequency (RF) signal to the other electrode.

As described above, a transducer array may be operated in a line-by-line manner in order to build up and ultrasound image. A 2D array possesses two directions in which a line-by-line imaging sequence may progress, meaning that it is possible to perform bi-plane imaging using a single array.

The CMUTs of the ultrasonic transducer array 55 may be connected to a first conductor 60 and a second conductor 61, which define a first element group 57a and a second element group 57b, respectively. In this example, the first conductor is connected to the second electrode 49 and the second conductor is connected to the first electrode 50. Each transducer connected by a common first or second conductor, i.e. an element group, define a line of the line-by-line imaging process.

When capturing the first imaging plane, the bias voltage may be provided to the first electrodes 50 of the CMUTs by way of the second conductors 61. The RF signal may then be provided to the second electrodes 49 of the CMUTs by way of the first conductors 60 in a line-by-line basis.

Similarly, when capturing the second imaging plane, the bias voltage may be provided to the second electrodes 49 of the CMUTs by way of the first conductors 60. The RF signal may then be provided to the first electrodes 50 of the CMUTS by way of the second conductors 61 in a line-by-line basis.

In the example shown in FIG. 5, the first and second imaging planes will be orthogonal to each other: however, it is possible to arrange the first ultrasonic transducer array in such a way as to generate first and second imaging planes having orientations other than orthogonal to each other.

Figures 6A, 6B:
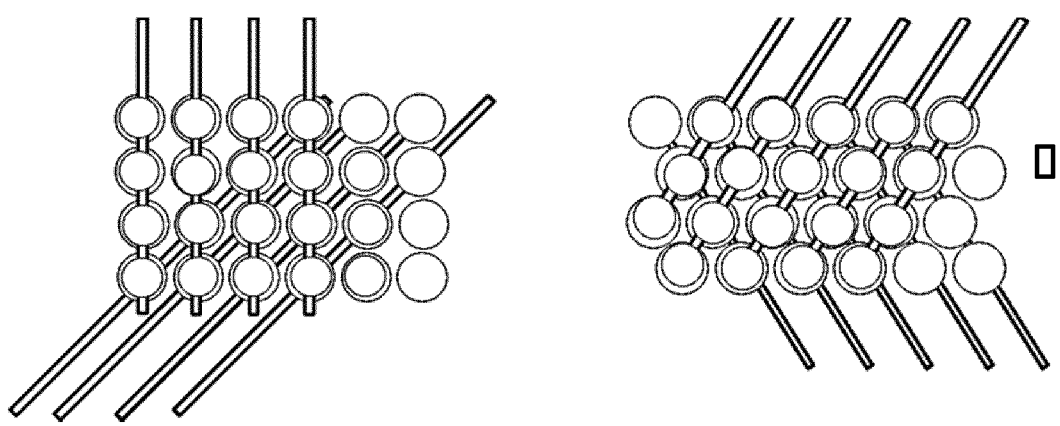
FIGS. 6a and 6b show alternative arrangements of the first ultrasonic imaging array shown in FIG. 5.

FIGS. 6a and 6b show examples of an ultrasonic transducer array capable of producing imaging planes at 45° and 60° to each other, respectively. As previously stated, the first and second element groups may take any angle between them according to the application of the system, such as: 90°; 60°; 45°; 30°; or 0°. The angle between the first and second ultrasound data will vary according to the angle between the first and second element groups.

The operation of the transducer die to generate two different views of an imaging region described above is visualized in FIG. 7.

Figure 7:
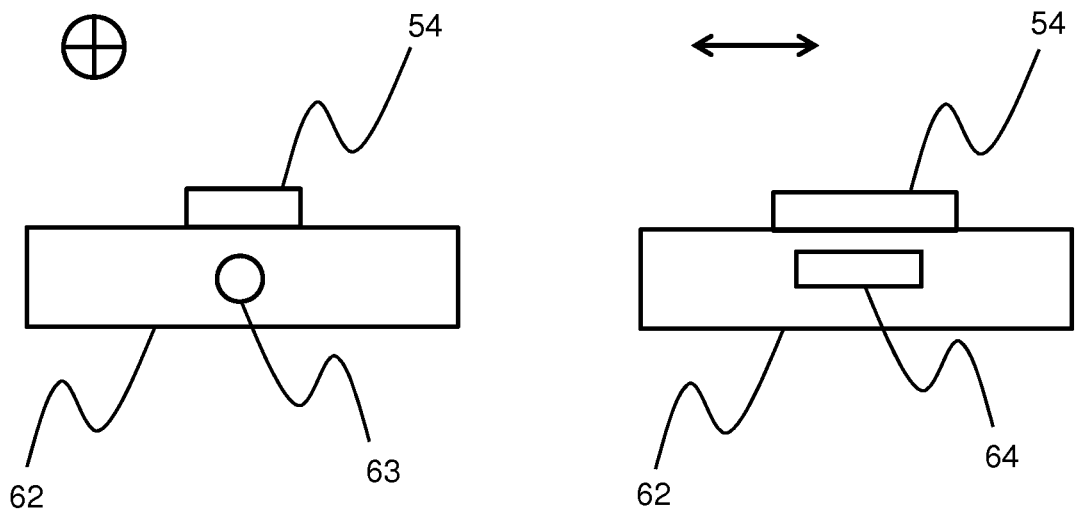
FIG. 7 shows an example of two views generated using the transducer die of FIG. 4.

FIG. 7 shows the transducer die 54 in contact with a subject 62.

When applying the bias voltage to the transducers 56 via the first conductors and the transmit/receive signal via the second conductors, a cross-sectional view 63 of the region of interest is generated. When the bias voltage is applied to the transducers via the second conductors and the transmit/receive signals are applied via the first conductors, a longitudinal view 64 of the region of interest is generated. For a transducer array such as the array shown in FIG. 5, the imaging planes of the cross-sectional view and the longitudinal view will be orthogonal to each other: whereas, the arrays shown in FIGS. 6a and 6b will produce images with planes orientated at 45° and 60° to each other, respectively.

Figure 8:
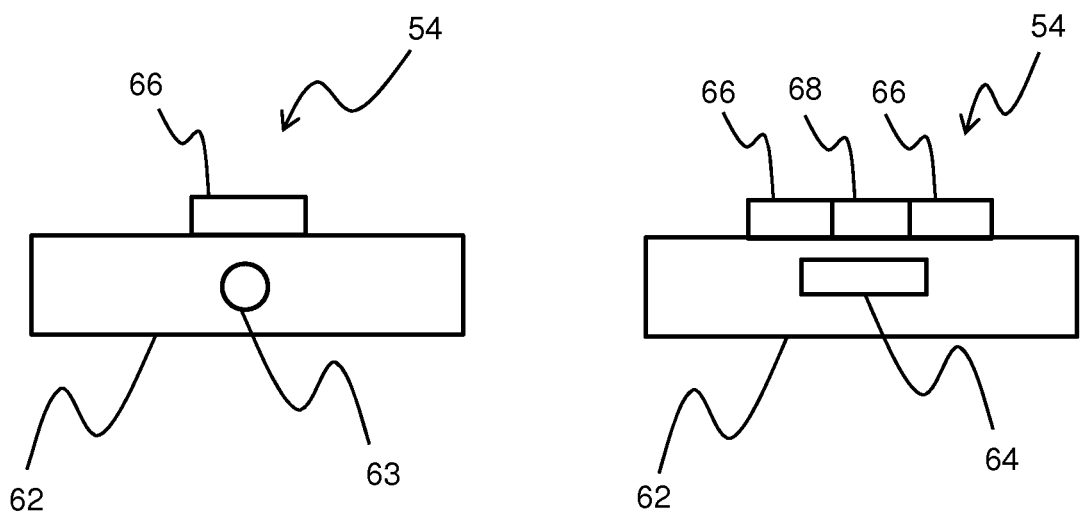
FIG. 8 shows a further example of views generated using the transducer die of FIG. 4, operated in a different mode to that used in FIG. 4.
Figure 8:
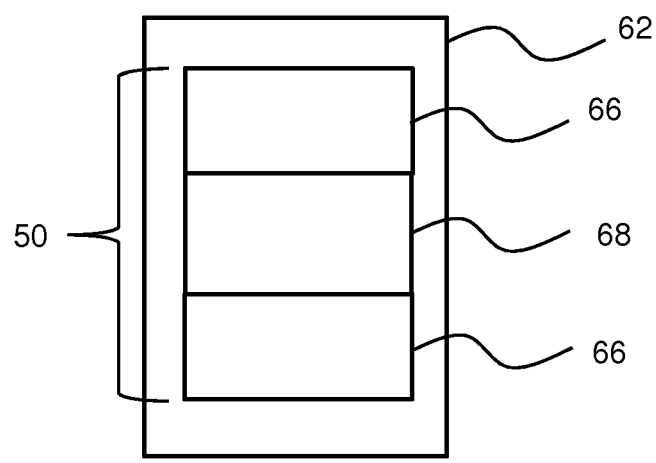

FIG. 8 shows an alternative method of operation of the transducer die 54 in contact with a subject 62.

In this example, the transducers 56 are separated into three sub-arrays defining two operational areas: a first biplane area 66; and a second biplane area 68, which may be employed to generate a cross-sectional view 63 and a longitudinal view 64, respectively.

By separating the transducer array 55 into the first and second biplane areas, it is possible to simultaneously generate both a cross-sectional view and a longitudinal view of the region of interest. In this example, the bias voltage is applied to the transducers of the first biplane areas 66 via the first conductors and the transmit/receive signals via the second conductors. Similarly, in this example, the bias voltage is applied to the transducers of the second biplane area 68 via the second conductors and the transmit/receive signals via the first conductors. Beam steering may be enabled by received/transmitted signals with different RF signal phases collected from/applied to each element (or sub-group of elements).

In this case, both the cross-sectional view and the longitudinal view may be available for viewing at the same time. For example, both views may be displayed to a user at the same time. Alternatively, the cross section view, for example, may be displayed to the user who may then indicate that they wish to view the longitudinal view. As both views are concurrently available, the change in view would happen immediately following the users instruction.

The two biplane images are obtained simultaneously in the sense that a scan of the full array of transducer elements generates both images, rather than performing a first scan with one configuration then performing a second scan with a new configuration.

Figure 9:
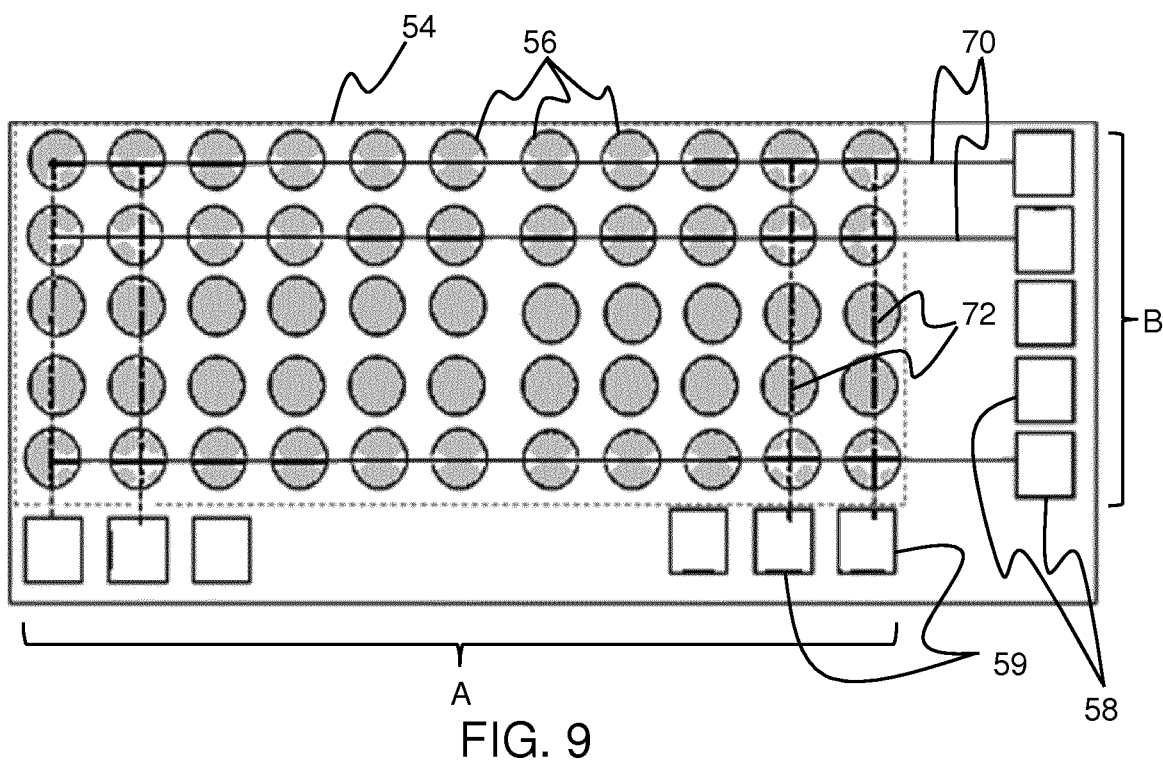
FIG. 9 shows a schematic representation of the transducer die of FIG. 4 indicating the first and second element groups of transducers.

FIG. 9 shows a schematic of the transducer die 54, wherein the transducers 56 are grouped into first and second element groups. As discussed above, the transducers need not be arrayed in a grid pattern and may be arranged in a dense packing pattern, a hexagonal packing pattern or any other suitable pattern.

The transducers of each first element group are connected to the first circuits 58 of side B by way of a first conductor 70 and the transducers of each second element group are connected to the second circuits 59 of side A by way of a second conductor 72. Each transducer forms part of both a first element group and a second element group and so is connected to both a first and second conductor.

Thus, when generating a cross section view of the imaging area, the bias voltage will be supplied from the first circuits 58 of side B by way of the first conductors 70 and the transmit/receive signals will be supplied from the second circuits 59 of side A by way of the second conductors. Similarly, when generating the longitudinal view of the imaging area, the bias voltage will be supplied by way of the second conductors and the transmit/receive signals will be supplied by way of the first conductors.

Figure 10:
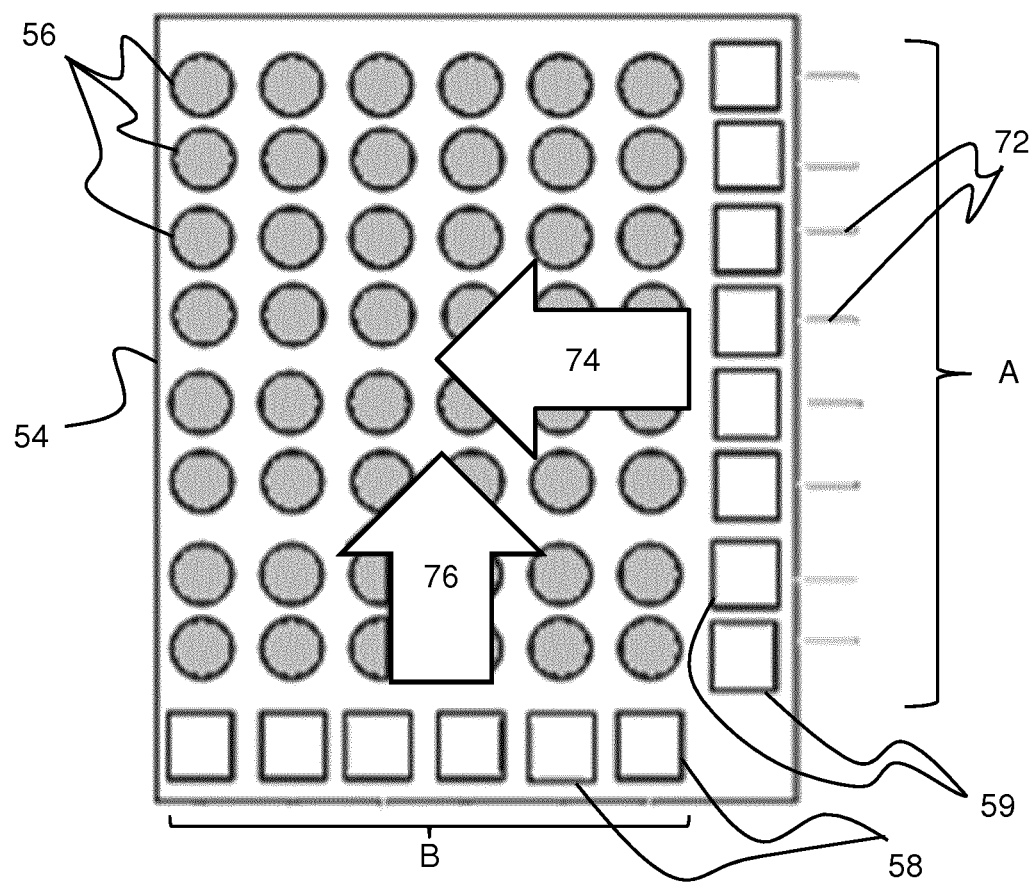
FIG. 10 shows a schematic representation of the transducer die of FIG. 4 indicating the direction in which image slices are obtained from the imaging region.

FIG. 10 illustrates the direction in which the first and second element groups are fired when generating the cross-sectional and longitudinal views in a line-by-line imaging cycle. It should be noted that the transducer die shown in FIG. 10 is rotated at 90° to the transducer die shown in FIG. 4.

When generating the cross-sectional view, the bias voltage is supplied from side B to the transducers by way of the first conductors and the transmit/receive signals supplied from side A by way of the second conductors. The first element groups are then activated line-by-line in direction 74 to build up the line-by-line cross-sectional image.

Similarly, when generating the longitudinal view, the bias voltage is supplied from side A to the transducers by way of the second conductors and the transmit/receive signals supplied from side B by way of the first conductors. The second element groups are then activated line-by-line in direction 76 to build up the line-by-line longitudinal image.

In this simplest implementation of the invention, there may be bias voltage circuits and transmit and receive circuits on both side A and side B, wherein the appropriate circuit is connected to the transducers by way of the column and row conductors depending on the desired view. However, this would double the amount of front and back-end hardware required to drive the transducer array.

Figure 11:
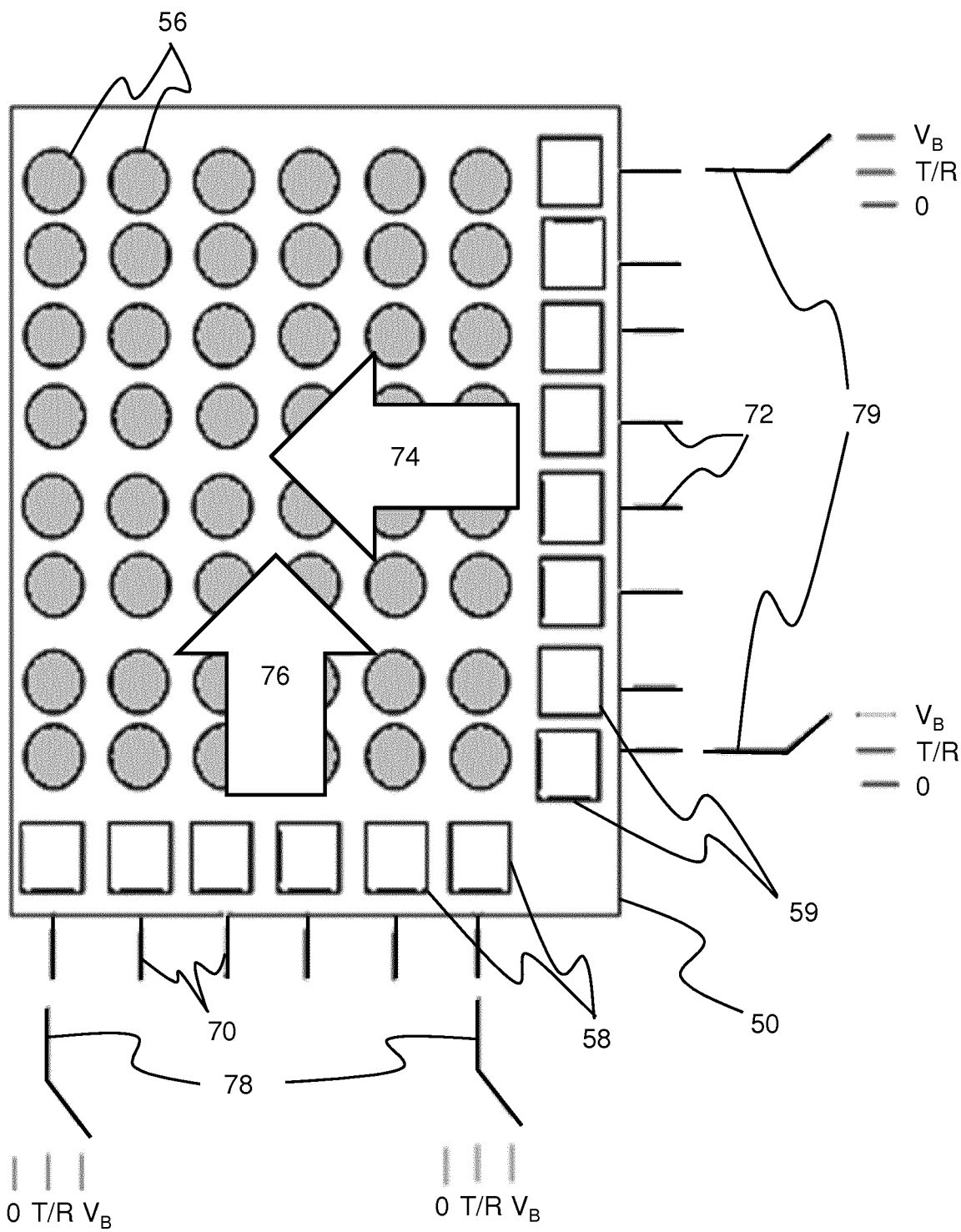
FIG. 11 shows a schematic representation of an alternate transducer die.

FIG. 11 shows an embodiment of the transducer die 54. It should be noted that the transducer die shown in FIG. 11 is rotated at 90° to the transducer die shown in FIG. 4.

In this example, the transducer die includes a set of first switches 78 connected to the transducers 56 by way of the first conductors 70 and a set of second switches 79 connected to the transducers by way of the second conductors 72. The switches allow the transducers to switch between being connected to the set of bias voltage circuits VB, thereby supplying the bias voltage to the transducers, or to the set of transmit and receive circuits T/R. Thus, it is possible to connect either the first conductors or the second conductors to the bias voltage circuits or the transmit and receive circuits without requiring a significant amount of additional hardware. The first and second switch implementations may be housed within the first 58 and second 59 circuits, respectively.

In addition, it is possible to provide an additional switch option 0, which causes the connected transducer to enter an idle state. In other words, the connected transducer is grounded. Thus, it is possible to dynamically alter the size of the transducer aperture by selectively deactivating transducers. A switch 78 may be a simple transistor made in Si processing and integrated into the transducer array itself. If a beam former is used close to the transducers, the switch may be integrated in the transducer die.

Figure 12:
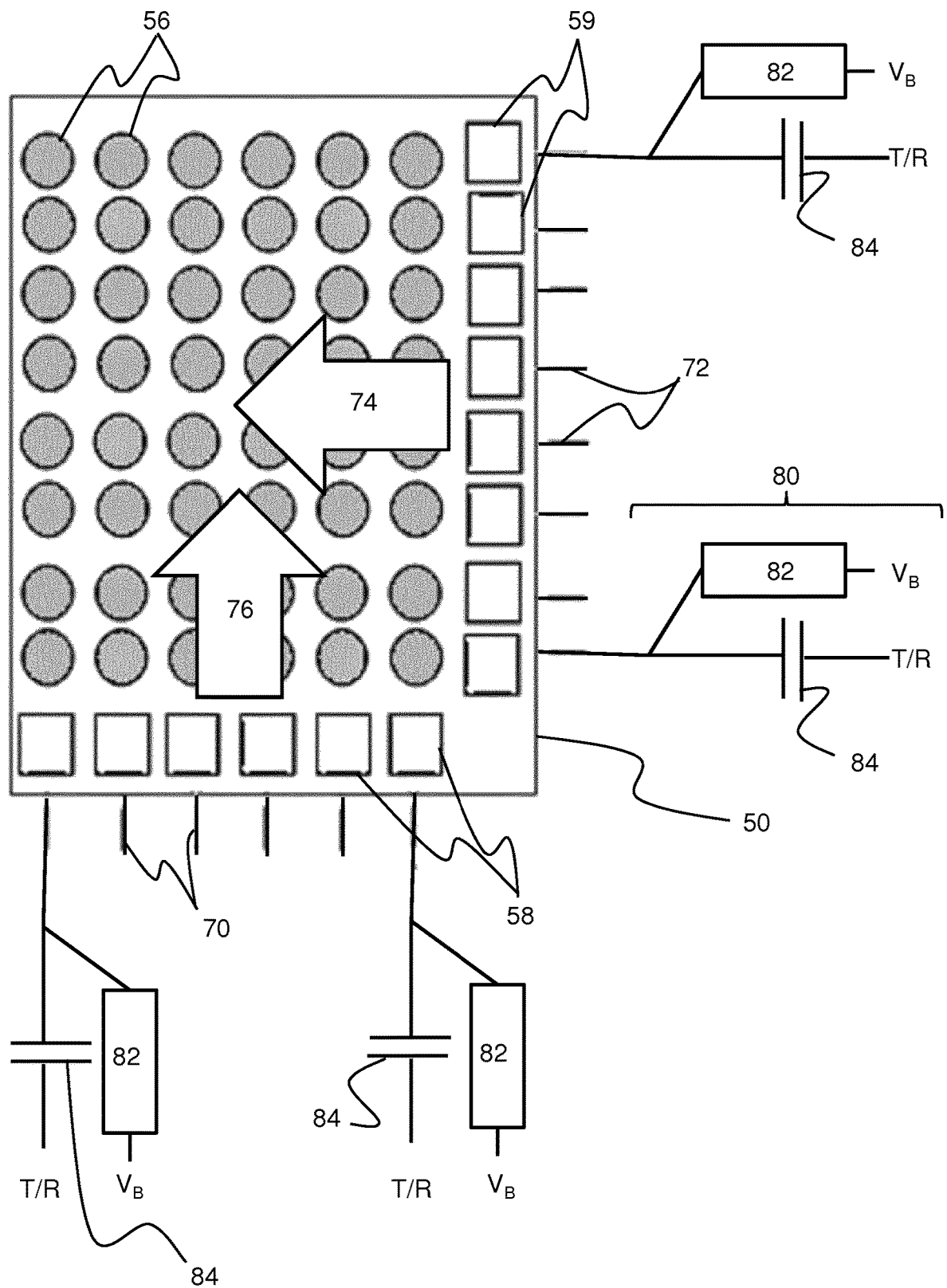
FIG. 12 shows a schematic representation of another alternate transducer die.

FIG. 12 shows a further embodiment of the transducer die 54. It should be noted that the transducer die shown in FIG. 12 is rotated at 90° to the transducer die shown in FIG. 4.

In this embodiment, the system includes a bias tee 80, which is a type of diplexer. A diplexer is a passive device that implements frequency-domain multiplexing. The bias tee comprises an inductor 82 and a capacitor 84. The branch of the bias tee connected to the bias voltage circuit VB forms the low-frequency arm and the branch connected to the transmit and receive circuits T/R forms the high-frequency arm.

The low-frequency arm is used to set the bias voltage, the high-frequency arm passes the radio frequency signals, which are supplied to and received from the transducers, but blocks the DC bias voltage. The remaining branch, connected to the transducers 56, passes both the bias voltage and radio frequency signals.

The bias tee 80 may be integrated on the same printed circuit board (PCB) as the transducer array 55 or within the transducers themselves. Alternatively, the bias tee may be integrated into the first 58 and second 59 circuits.

The bias voltage and the transmit/receive signal be applied on the same conductor using a bias tee, in which case the other conductor is connected to ground. In other words, it is possible to perform the bi-plane imaging by providing both the bias voltage and the RF signals to the transducers via the first conductor (for the first view) or the second conductor (for the second view).

Figure 13:
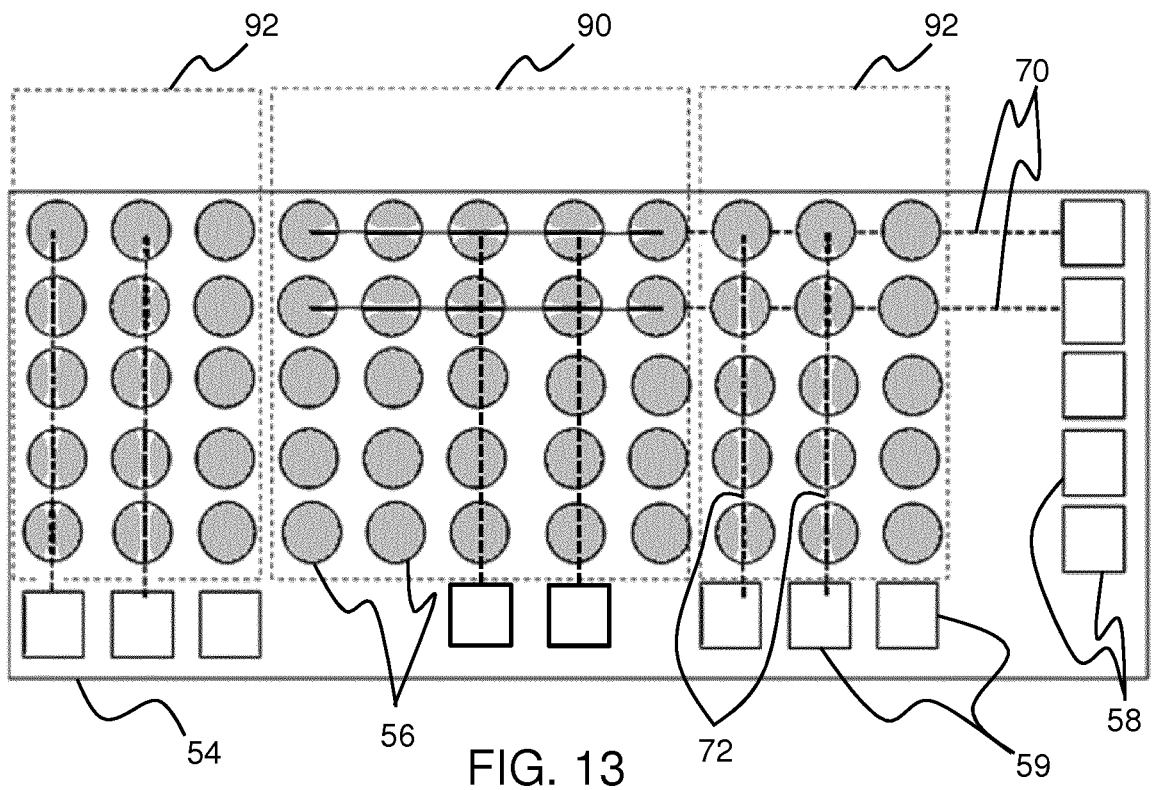
FIG. 13 shows a schematic representation of a transducer die divided into sub-arrays.

FIG. 13 shows an embodiment of the transducer die 54, wherein the transducers 56 are divided into sub-arrays.

As described above, each transducer 56 belongs to both a first element group and a second element group and so is connected to a first conductor 70 and a second conductor 72, which may provide either the bias voltage or the transmit/receive signals. By providing a sub-array with the bias voltage via the first conductors 70 and the transmit and receive signals via the second conductors 72, said sub-array will generate a cross-sectional view of the imaging region. Similarly, by providing a sub-array with the bias voltage via the second conductors 72 and the transmit and receive signals via the first conductors 70, said sub-array will generate a longitudinal view of the imaging region. In other words, it is possible to divide the transducer die into multiple sub-arrays, which may capture different views based on how the bias voltage and transmit/receive signals are provided to the element groups of said sub-arrays.

In the example shown in FIG. 13, the transducer die 54 is separated into one longitudinal sub-array 90 and two cross-sectional sub-arrays 92. By dividing the die into dedicated areas, such as those shown in FIG. 13, it is possible to generate a simultaneous biplane view: In other words, both a cross-sectional and a longitudinal view may be available at the same time.

Figure 14:
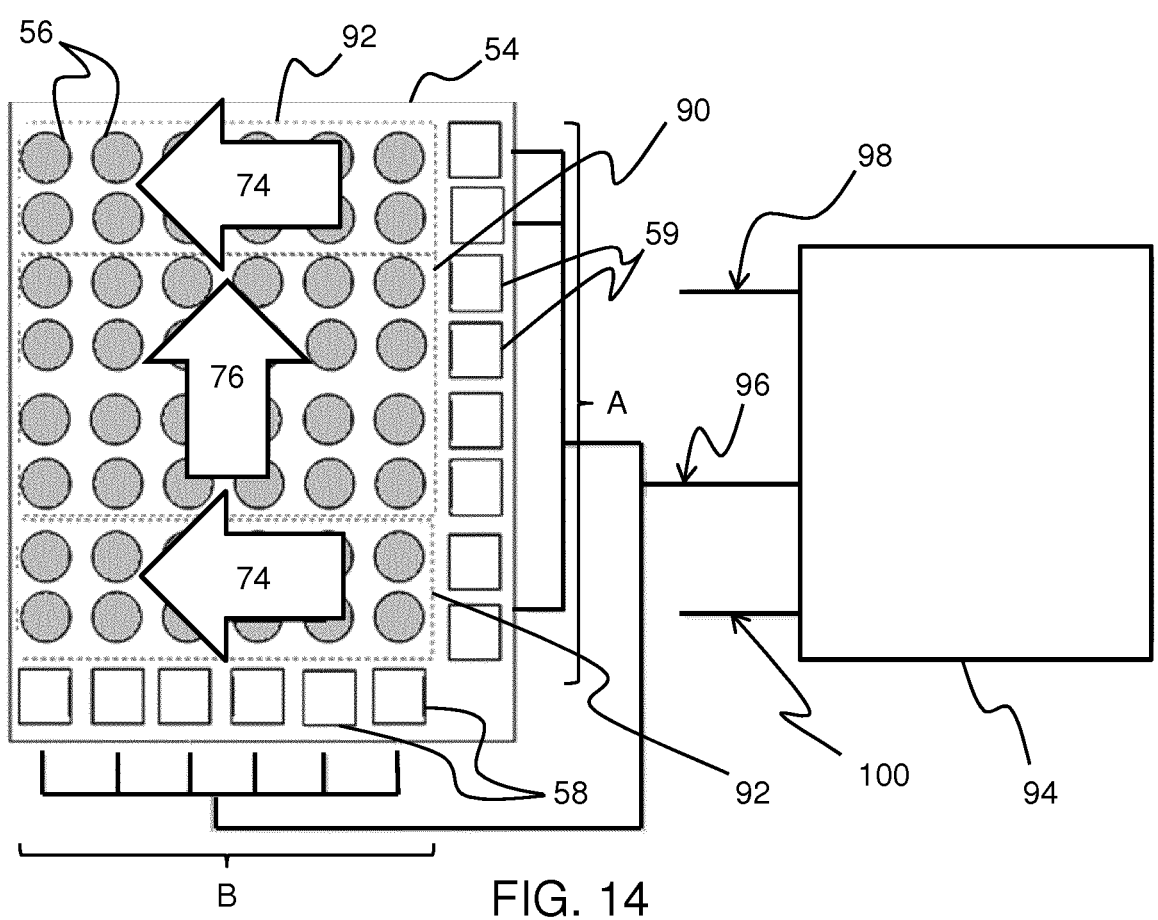
FIG. 14 shows an example of the transducer die of FIG. 13 operated using bias switching.

FIG. 14 shows an implementation of the transducer die 54 of FIG. 13, wherein the transducer array is divided into one longitudinal sub-array 90 and two cross-sectional sub-arrays 92. It should be noted that the transducer die shown in FIG. 14 is rotated at 90° to the transducer die shown in FIG. 4.

In the example shown in FIG. 14, the bias voltage is selectively provided to either the first or second conductors in order to form the sub-arrays. The set of bias voltage circuits and the set of transmit and receive circuits are represented by a circuit block 94. The transmit and receive signals may be transferred to and from the transducers by way of a T/R line 96, which is to connected to the first circuits 58 of side B and the second circuits 59 of side A.

A bias voltage is supplied to side B, and so the first conductors, of the cross-sectional sub-arrays 92 by way of a first bias voltage line 98. Similarly, a bias voltage is supplied to side A, and so the second conductors, of the longitudinal sub-array 90 by way of a second bias voltage line 100.

The element groups of the cross-sectional sub-arrays 92 may then, for example, be fired by way of the transmit signal, which is supplied by the set of transmit and receive circuits, in a line-by-line manner in direction 74. The element groups of the longitudinal sub-array 90 may, for example, be fired by way of a transmit signal, which is supplied by the set of transmit and receive circuits, in a line-by-line manner in direction 76.

Figure 15:
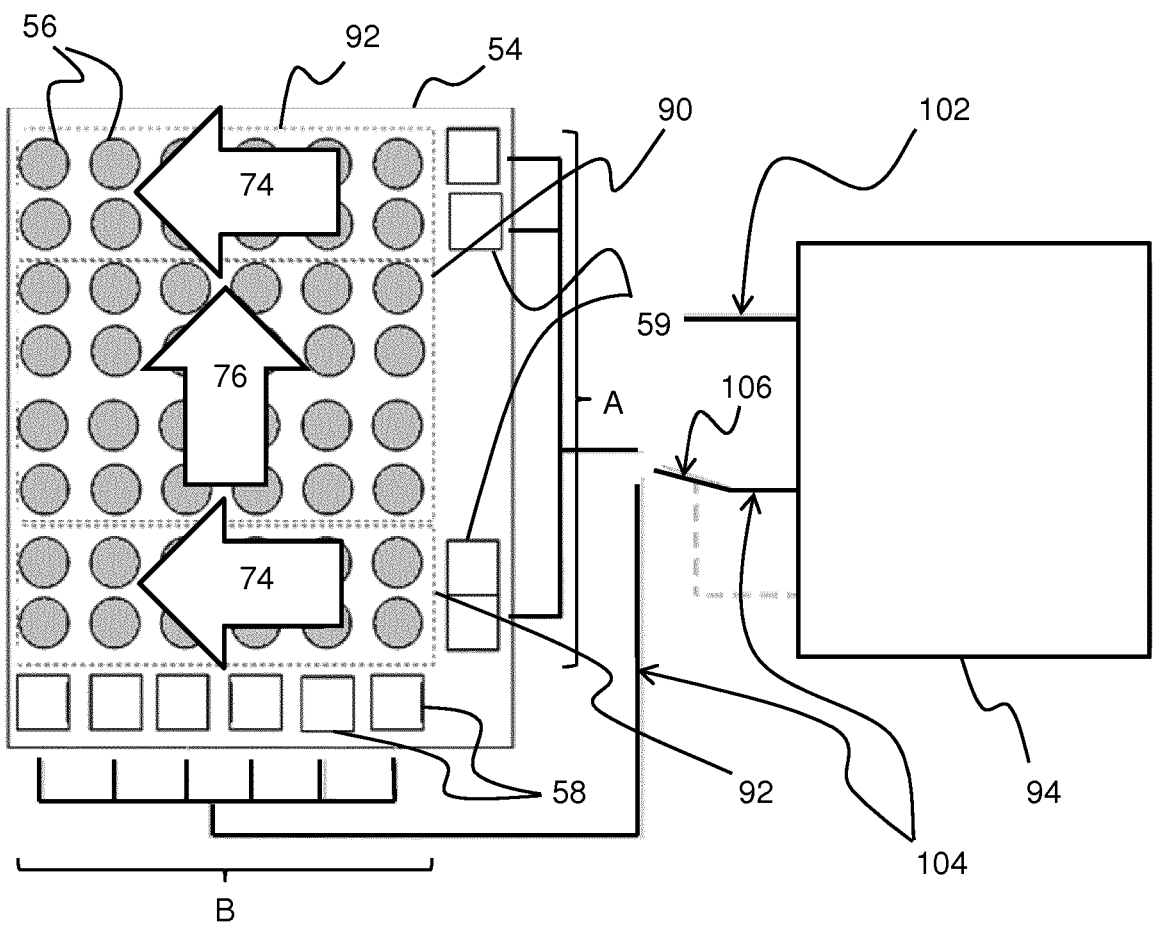
FIG. 15 shows an example of the transducer die of FIG. 13 operated using transmit and receive signal switching.

FIG. 15 shows an alternative implementation of the transducer die 54 of FIG. 13, wherein the transducers 56 are grouped into one longitudinal sub-array 90 and two cross-sectional sub-arrays 92. It should be noted that the transducer die shown in FIG. 15 is rotated at 90° to the transducer die shown in FIG. 4.

In the example shown in FIG. 15, the transmit and receive signals are selectively provided to either the first or second conductors in order to form the sub-arrays. The bias voltage is provided to both sides A and B of the transducer die by way of a bias voltage line 102.

The set of transmit and receive circuits may be connected to either side A or side B by way of a T/R line 104, wherein the T/R line comprises a switch 106 adapted to provide the transmit signals to side A or side B depending on which sub-array is being driven. For example, if a line of transducers of the longitudinal sub-array is being activated, the transmit and receive circuits may be connected to side A: whereas, if a line of the transducers of the cross-sectional sub-arrays is being activated, the transmit and receive circuits may be connected to side B of the transducer die.

Figure 16:
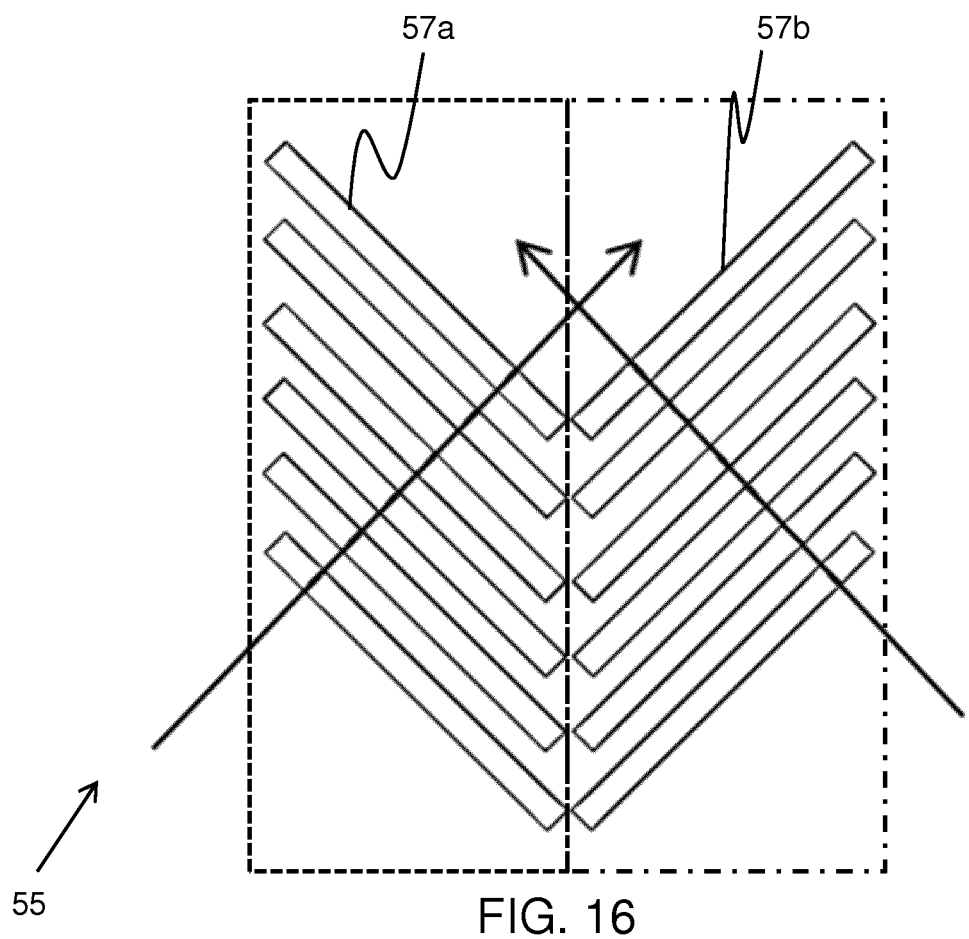
FIG. 16 shows a transducer die wherein the first and second element groups are arranged in a Fishbone layout.

FIG. 16 shows a further embodiment of the transducer arrays wherein the first element groups 57a and the second element groups 57b are arranged in a fishbone pattern.

The examples described above refer to a system having a single transducer array. It is possible to operate multiple arrays according to the methods described above, each contained in the same arrangement, for example an ultrasonic probe having multiple arrays. The multiple arrays may have element groups having different orientations. For example, the first and second element groups of a first array may be orthogonal to each other: whereas, the first and second element groups of a second array may have an angle of 45° between each other. In this way, a single ultrasound probe may acquire ultrasound data from four different views.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound method for performing ultrasound data acquisition using an array of transducer elements, wherein the transducer elements of the array are capacitive micromachined ultrasound transducers (CMUTs), wherein each CMUT comprises only two electrodes, a first electrode and a second electrode separated by a cavity, the transducer elements being grouped into transducer element groups with a set of first conductors with a respective first conductor shared between transducer elements in each of a plurality of first element groups having a first orientation, wherein the respective first conductor is connected to the first electrode of each element of a respective first transducer element group, and a set of second conductors with a respective second conductor shared between transducer elements in each of a plurality of second element groups having a second orientation different from the first orientation, wherein the respective second conductor is connected to the second electrode of each element of a respective second transducer element group, wherein the method comprises generating time sequentially:

first ultrasound data by connecting the element groups of the array or the element groups of a sub-array of the element groups to a first bias voltage circuit ($V_B$) by the respective first conductor, in which all of the transducer elements of the array are activated by the first bias voltage circuit via each respective first conductor and connected to a transmit and receive circuit (T/R) via each respective second conductor; and second ultrasound data by connecting the element groups of the array or the element groups of the sub-array of the element groups to a second bias voltage circuit by the respective second conductor, in which all of the transducer elements of the array are activated by the second bias voltage circuit via each respective second conductor and connected to the transmit and receive circuit by each respective first conductor, wherein each respective first conductor is associated with a first circuit, said first circuit being arranged to connect the respective first conductor to the first bias voltage circuit through a first inductor and to the transmit and receive circuit (T/R) through a second capacitor, and each respective second conductor is associated with a second circuit, said second circuit being arranged to connect the respective second conductor to the second bias voltage circuit through a second inductor and to the transmit and receive circuit through a second capacitor.

2. An ultrasound method for performing ultrasound data acquisition using an array of transducer elements, wherein the transducer elements of the array are capacitive micromachined ultrasound transducers (CMUTs), wherein each CMUT comprises only two electrodes, a first electrode and a second electrode separated by a cavity, the transducer elements being grouped into transducer element groups with a set of first conductors with a respective first conductor shared between transducer elements in each of a plurality of first element groups having a first orientation, wherein the respective first conductor is connected to the first electrode of each element of a respective first transducer element group, and a set of second conductors with a respective second conductor shared between transducer elements in each of a plurality of second element groups having a second orientation different from the first orientation, wherein the respective second conductor is connected to the second electrode of each element of a respective second transducer element group, wherein the method comprises:

generating first ultrasound data by connecting the element groups of the array or the element groups of a sub-array of the element groups to a first bias voltage circuit ($V_B$) by the respective first conductor; and generating second ultrasound data by connecting the element groups of the array or the element groups of the sub-array of the element groups to a second bias voltage circuit by the respective second conductor, wherein the method further comprises simultaneously activating the respective first transducer element group and the respective second transducer element group, thereby simultaneously acquiring the first ultrasound data and the second ultrasound data.

* * * * *